US012734320B2

(12) United States Patent
Göbel

(10) Patent No.: US 12,734,320 B2
(45) Date of Patent: *Sep. 15, 2026

(54) DEVICE AND METHOD FOR THE DYNAMICALLY SEALING OCCLUSION OR SPACE-FILLING TAMPONADE OF A HOLLOW ORGAN

(71) Applicant: Advanced Medical Balloons GmbH, Waghäusel (DE)

(72) Inventor: Fred Göbel, Lützelbach (DE)

(73) Assignee: Advanced Medical Balloons GmbH, Waghäusel (DE)

( * ) Notice: Subject to any disclaimer, the term of this patent is extended or adjusted under 35 U.S.C. 154(b) by 1247 days.

This patent is subject to a terminal disclaimer.

(21) Appl. No.: 17/533,691

(22) Filed: Nov. 23, 2021

(65) Prior Publication Data

US 2022/0080141 A1 Mar. 17, 2022

Related U.S. Application Data

(63) Continuation-in-part of application No. 15/533,151, filed as application No. PCT/IB2015/002309 on Dec. 4, 2015, now Pat. No. 11,207,482.

(30) Foreign Application Priority Data

Dec. 4, 2014 (DE) ..................... 10 2014 017 872.2
Jan. 22, 2015 (DE) ..................... 10 2015 000 621.5

(Continued)

(51) Int. Cl.
*A61M 16/04* (2006.01)
*A61M 25/10* (2013.01)

(52) U.S. Cl.
CPC ...... *A61M 16/044* (2013.01); *A61M 16/0486* (2014.02); *A61M 25/10186* (2013.11)

(58) Field of Classification Search
CPC ............ A61M 16/044; A61M 16/0486; A61M 16/0445; A61M 16/0459; A61M 25/1018;
(Continued)

(56) References Cited

U.S. PATENT DOCUMENTS 3,794,043 A * 2/1974 McGinnis ........... A61M 16/044 137/853
4,159,722 A * 7/1979 Walker ............ A61M 25/10185 604/920

(Continued)

FOREIGN PATENT DOCUMENTS

WO WO-2004004801 A2 * 1/2004 ........ A61M 25/1006
WO WO 2013/139986 9/2013

OTHER PUBLICATIONS

Badenhorst, Changes in Tracheal Cuff Pressure in Respiratory Support, Critical Care Medicine 15(4), 1987, pp. 300-302.

(Continued)

*Primary Examiner* — Joseph D. Boecker
*Assistant Examiner* — Brian T Khong
(74) *Attorney, Agent, or Firm* — McDonnell Boehnen Hulbert & Berghoff LLP

(57) ABSTRACT

A device for dynamically sealing intubation of a hollow organ is disclosed. The device includes a shaft-shaped tube configured to be inserted into the hollow organ. The shaft-shaped tube has a primary lumen that provides access through the hollow organ or to the hollow organ. The device includes an intracorporeal sealing balloon that surrounds a distal region of the shaft-shaped tube. The intracorporeal sealing balloon is configured to operate as a cuff that dynamically seals the hollow organ. One or more secondary lumens for filling the intracorporeal sealing balloon are integrated into a wall of a proximal region of the shaft-shaped tube.

24 Claims, 7 Drawing Sheets

(30) Foreign Application Priority Data

Jan. 29, 2015 (DE) ..................... 10 2015 001 030.1
Mar. 4, 2015 (DE) ..................... 10 2015 002 995.9
Nov. 18, 2015 (DE) ..................... 10 2015 014 824.9

(58) Field of Classification Search
CPC ...... A61M 25/10184; A61M 25/10185; A61M 25/10186; A61M 25/10187; A61M 25/10188; A61M 2025/102; A61M 2025/1022; A61M 2205/07; A61M 2205/3341; A61M 2205/3344; A61M 2205/3331; A61M 2016/0027
See application file for complete search history.

(56) References Cited

U.S. PATENT DOCUMENTS 4,285,340 A 8/1981 Gezari et al.
4,649,914 A * 3/1987 Kowalewski ..... A61M 16/0445 417/570
4,762,129 A 8/1988 Bonzel
4,770,170 A 9/1988 Sato et al.
5,024,668 A * 6/1991 Peters ................ A61M 1/3643 600/18
5,029,591 A * 7/1991 Teves ................... A61M 16/04 128/207.15
5,188,592 A * 2/1993 Hakki .................. A61M 25/10 604/35
5,218,970 A * 6/1993 Turnbull ................. A61B 5/03 600/595
5,361,753 A * 11/1994 Pothmann ........... A61M 16/021 128/207.15
5,947,927 A 9/1999 Mertens
6,802,317 B2 10/2004 Göbel
8,393,328 B2 3/2013 Angel et al.
2003/0066532 A1* 4/2003 Gobel ............... A61M 16/0445 128/200.26
2007/0255160 A1* 11/2007 Daly ................ A61M 16/0003 600/529
2007/0277830 A1 12/2007 Ladru et al.
2010/0252048 A1* 10/2010 Young ................ A61M 16/024 128/207.15
2010/0319702 A1* 12/2010 Wood ............... A61M 16/0443 128/207.14
2011/0109458 A1* 5/2011 Shipman ............ A61M 16/044 128/207.14
2012/0145159 A1 6/2012 Yamada
2013/0146062 A1 6/2013 Schumacher et al.

OTHER PUBLICATIONS

Bassi, An In Vitro Study to Assess Determinant Features Associated With Fluid Sealing in the Design of Endotracheal Tube Cuffs and Exerted Tracheal Pressures, Critical Care Medicine 41(2), 2013, pp. 518-526.

* cited by examiner

3
G,S
OD
ID
5

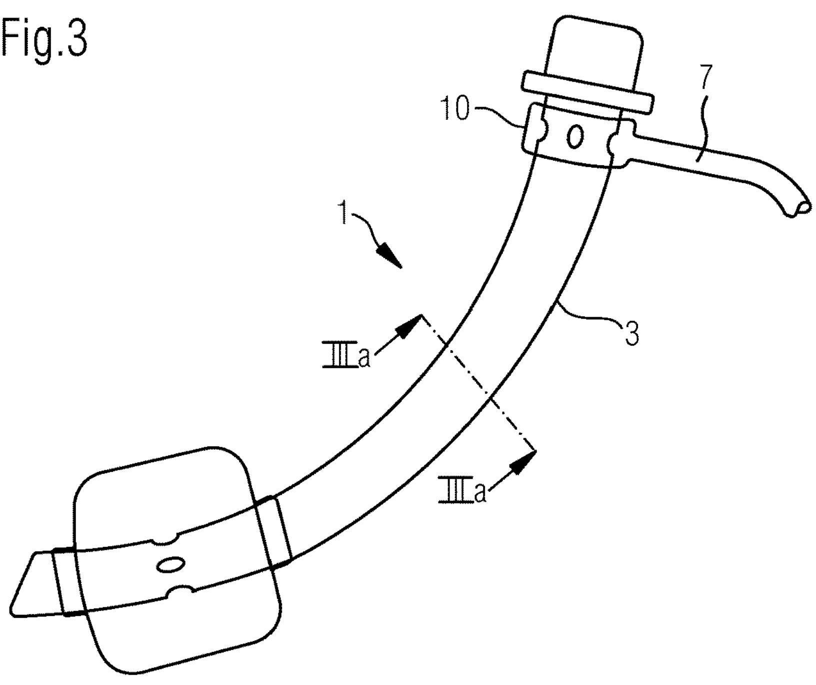
Fig.3a
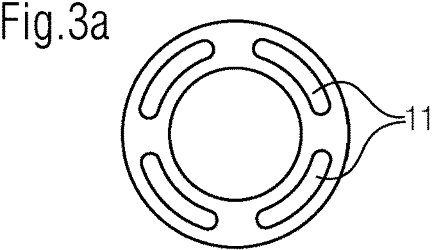
Fig.4
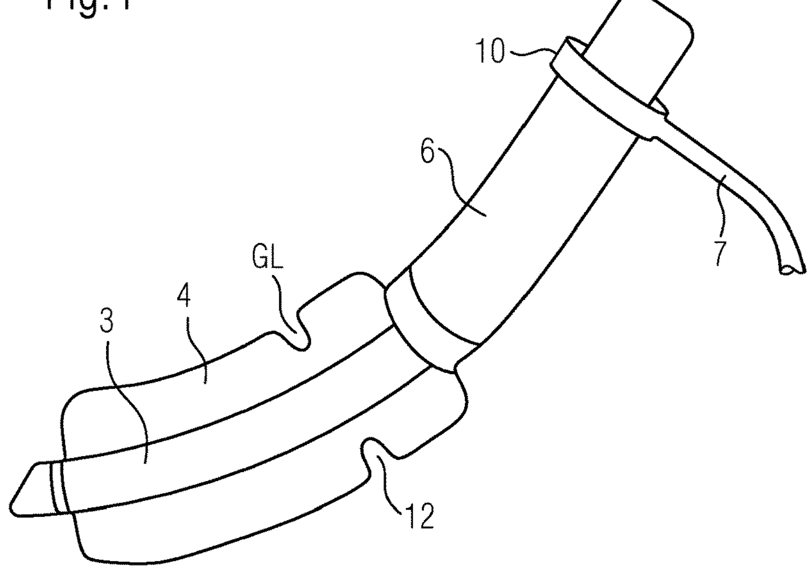

20
22
RE
SW
K
22
4
21
36
38
37
7
34
M
24''
31
32
33
35
M
24(3)

Fig.11a
$$y(t) = Kp \bullet e(t) + Kd\frac{de(t)}{dt}$$
Fig.11c
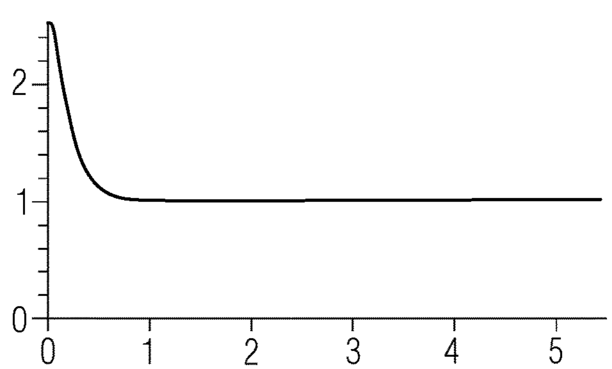
Fig.11b
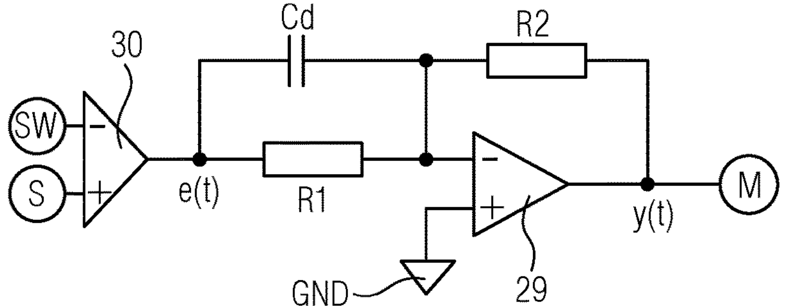
Fig.11d
$$Kp = \frac{R1}{R2}$$
$$Kd = R2 \bullet Cd$$

DEVICE AND METHOD FOR THE DYNAMICALLY SEALING OCCLUSION OR SPACE-FILLING TAMPONADE OF A HOLLOW ORGAN

REFERENCE TO PENDING PRIOR PATENT APPLICATIONS

This patent application:

(i) is a continuation-in-part of pending prior U.S. patent application Ser. No. 15/533,151, filed Jun. 5, 2017 by Creative Balloons GmbH for DEVICE AND METHOD FOR THE DYNAMICALLY SEALING OCCLUSION OR SPACE-FILLING TAMPONADE OF A HOLLOW ORGAN, which patent application, in turn:

(a) claims benefit of International (PCT) Patent Application No. PCT/IB2015/002309, filed Dec. 4, 2015 by Fred Göbel and Creative Balloons GmbH for DEVICE AND METHOD FOR THE DYNAMICALLY SEALING OCCLUSION OR SPACE-FILLING TAMPONADE OF A HOLLOW ORGAN, which in turn claims benefit of:

(1) German Patent Application No. DE 10 2014 017 872.2, filed Dec. 4, 2014;

(2) German Patent Application No. DE 10 2015 000 621.5, filed Jan. 22, 2015;

(3) German Patent Application No. DE 10 2015 001 030.1, filed Jan. 29, 2015;

(4) German Patent Application No. DE 10 2015 002 995.9, filed Mar. 4, 2015; and (5) German Patent Application No. DE 10 2015 014 824.9, filed Nov. 18, 2015.

The seven (7) above-identified patent applications are hereby incorporated herein by reference.

FIELD OF THE INVENTION

The invention is directed to a device and a method for the dynamic occlusion or tamponade of a hollow organ by means of a balloon-like element, in particular for the dynamic, aspiration-preventing seal of the intubated trachea in patients who are breathing independently and in patients in a machine-assisted spontaneous ventilation mode.

BACKGROUND OF THE INVENTION

In many cases, the continuous motility of the organ itself is a fundamental problem associated with the sealing closure or space-filling tamponade of organs or cavities with a fillable, balloon-like element in a way that is gentle to the organ and efficient. Organs or body cavities that are limited by musculo-connective tissue often have autonomous motility or are subjected to the dynamics of adjacent organs or structures. In order to create a continuous seal of the organ lumen, autonomous or correspondingly motile organs require a particular regulating mechanism that reacts quickly to fluctuations in the organ diameter or changes in the tone of the organ wall. As the changes in diameter or tone occur, said mechanism must act as a synchronously as possible.

The problem of dynamic, synchronized adaptation of a balloon occlusion of a hollow organ can be illustrated with the example of the human trachea. The trachea is a tube-like structure with portions composed of cartilaginous tissue, connective tissue and muscle. It extends from the lower section of the larynx to the branching of the main bronchi. The front and side portions of the trachea are stabilized by clip-like, approximately horseshoe-shaped structures, which in turn are connected to each other in the longitudinal direction by connective tissue-like layers of tissue. The trachea lumen is closed off on the rear-wall side by the so-called pars membranacea, which consists of material made of continuous musculo-connective tissue, without any reinforcing cartilaginous elements. The esophagus, which is made of musculo-connective tissue, lies on its dorsal side.

The upper quarter of the trachea is usually located outside of the thorax, while the two lower three quarters lie within the thoracic cavity delimited by the thorax and diaphragm. The lower thoracic portion of the trachea is thereby especially subjected to the pressure fluctuations in the thoracic cavity that occur as part of the thoracic respiratory mechanics of a spontaneously breathing patient as well as a patient who is spontaneously breathing with assistance.

When the patient breathes in, the thoracic volume is enlarged by the lifting of the ribs and simultaneous lowering of the diaphragm, and the intrathoracic pressure therefore decreases. As a result of respiratory mechanics, this drop in pressure leads to the inflow of inhaled air into the lungs, which expands with the increase in thoracic volume.

However, the pressure drop in the thorax associated with the increase in thoracic volume also leads to corresponding drops in pressure within filled balloon elements positioned in the patient's thorax. Balloon elements such as these are used in tracheal tubes and tracheostomy cannulas, for example, to seal the deep airways against inflowing secretions from the throat and to permit positive pressure ventilation of the patient's lungs. The cyclical drops in thoracic pressure caused by the patient's own breathing can move the sealing pressure in the balloons of ventilation catheters into low ranges, in which a sufficient seal against secretions that collect in the trachea above the sealing balloon (cuff) is no longer ensured. See Badenhorst C H, Changes in tracheal cuff pressure in respiratory support, Crit Care Med, 1987; 15/4: 300-302.

Whereas the sealing performance of conventional PVC tracheal tube cuffs correlates very closely with the effective filling pressure in the cuff, the especially thin-walled polyurethane tracheal tube cuffs demonstrate significantly more stable sealing efficiency when the tracheal sealing pressures fall into ranges around 15 mbar. See Bassi G L, Crit Care Med, 2013; 41: 518-526.

Of particular importance for the secretion seal of tracheal sealing balloons, however, is the pressure range from 5 to 15 mbar, which is easily achieved during the independent breathing of a patient, essentially from breath to breath. Seal-optimized ventilation catheters with micro-thin-walled PUR cuffs can also still ensure good sealing performance at ca. 10 mbar filling pressure. However, they cannot protect against inflowing, infectious secretions during pressure drops below 10 mbar to sub-atmospheric thoracic pressure values.

No sealing technology is yet available for sealing the trachea by means of a cuff-like sealing balloon, which synchronizes with the breathing effort of the thorax, is atraumatic, seals efficiently over sufficiently wide ranges of filling pressure and is cost-effective to manufacture. Although many different technical embodiments of filling pressure-regulating devices for tracheal ventilation catheters are described in the prior art, a sufficiently synchronized adaptation of the sealing pressure to alternating thoracic pressures, as are observed in autonomous breathing in patients, has not yet been achieved.

In the known ventilation catheters, the trachea-sealing balloon element is usually filled by small-bore filling lines which are extruded into the shaft of the catheter. The small cross-sections of the filling lines generally do not ensure a flow rate of the filling medium which fills the balloon that is sufficiently strong to maintain a tracheal seal during the drop in thoracic pressure. Even technically complicated extracorporeal control mechanisms, such as the CDR 2000 device produced by Logomed GmbH (no longer commercially available), function inadequately because of the small-bore supply lines between the sealing balloon element and the regulator.

SUMMARY OF THE INVENTION

The present invention describes a novel catheter technology that permits a quick flow rate between a regulating mechanism outside the body and a balloon-like sealing element placed in the trachea by means of an especially flow-efficient supply line for the filling medium. Technologically simple and cost-effective means are used to compensate for the cuff volume in a way that is sufficiently synchronized for the dynamic sealing of the trachea of a spontaneously breathing patient and that maintains the seal.

Especially, the invention describes a device for the dynamically sealing intubation of a hollow organ, comprising a tube in the form of a shaft that can be inserted into the hollow organ, with a primary lumen to provide access through or to the hollow organ in question, and comprising an intracorporeal sealing balloon, which surrounds a distal region of the shaft of said tube in the manner of a cuff for the purpose of sealing it against the hollow organ, wherein one or more secondary lumens for filling said intracorporeal sealing balloon are integrated into the wall of at least a proximal region of said shaft, wherein, within each cross-sectional plane that is intersected perpendicularly by the local longitudinal direction of the device, the following applies for the overall interior cross-section Q1 of the primary lumen and the sum Q2 of the interior cross-sections of all secondary lumens:

$$Q2/(Q1+Q2) \geqq 0.06,$$

wherein at an extracorporeal filling tube, which communicates with all secondary lumens, a control device is provided in order to keep the pressure within the intracorporeal sealing balloon nearly constant in such a way that a) when the volume of the hollow organ increases, a corresponding amount of the filling medium is forced to flow into the intracorporeal sealing tube in order to increase the volume of the intracorporeal sealing tube accordingly, and b) when the volume of the hollow organ decreases, a corresponding amount of the filling medium is allowed to flow out of the intracorporeal sealing tube in order to decrease the volume of the intracorporeal sealing tube accordingly.

The invention further describes a thin-walled ventilation catheter shaft that has a single lumen and a shaft wall that is preferably stabilized by a corrugated tube-like corrugation. The corrugation of the shaft permits especially low wall thicknesses, which optimally allows for large inner lumens for the particularly low-resistance breathing of the patient. The corrugation additionally gives the shaft a particular low-tension or non-elastic axial flexibility and thus adaptability in the trachea of a spontaneously breathing patient. A flexible shaft such as this can additionally be made of especially hard PUR types, which then permit particularly thin wall thicknesses.

One possible embodiment of the invention is based on a balloon element which is fixedly and sealingly attached to the supporting shaft body at the distal end of the ventilation catheter and the proximal end of which narrows almost to the outer dimensions of the catheter shaft, but leaves a coaxial gap for the shaft. This proximal extension of the balloon can extend into the thoracic section of the trachea, but can also be guided into the extra-thoracic sections of the trachea as far as the region of the vocal cords or also to the lower region of the throat, wherein a particular free gap is formed between the sleeve of the proximal balloon segment that narrows in this way and the enclosed shaft.

The gap created in this way permits an especially large-bore, efficient volume flow between a volume reservoir disposed outside the body and the trachea-sealing balloon element. The gap further prevents potentially damaging direct contact by the corrugated catheter shaft with the epithelium of the trachea.

The concentric arrangement of the catheter shaft in a tapering, tube-like proximal balloon-segment is advantageous especially in the region of the vocal cords. Here, the balloon envelope that encloses the shaft rests against the vocal cords in a protective way and prevents abrasive effects by the shaft when it moves relative to the respiratory tract.

In the proximal section of the tracheal ventilation catheter, the end of the tube-like tapered balloon segment is preferably accommodated by a multi-lumen shaft element. This shaft element preferably has a supply line cross-section whose flow-affecting cross-section preferably corresponds to the flow-affecting cross-section of the gap between the shaft and the proximal balloon segment. A filling tube then attaches to the supply lumen integrated into the proximal catheter, said filling tube having a diameter with corresponding flow characteristics to those ensured within the catheter.

The invention shows an example of a method of calculating the dimensions of the claimed gap created between the catheter shaft and the proximal extension of the balloon end or balloon body, which provides a good approximation of how large the radial gap must be in order to achieve a sufficiently compensating volume flow between the regulator and balloon in under 10 milliseconds after thoracic pressure begins to decrease.

Both the proximal balloon segment surrounding the shaft and the distal balloon segment sealing the trachea are preferably produced from a material that is as thin-walled as possible and only slightly elastic. In this way, the required dimensional stability of the balloon body is ensured when it is loaded with filling pressure from the inside or under mechanical stress from the outside.

The invention further describes various methods for quickly sealing the trachea in a volume-compensating way, wherein a claimed catheter provided with an occluding or tamponading balloon element is connected to an extracorporeal regulator device. By coupling the catheter with the regulator, an interior space is created that can be charged with isobaric filling pressure.

The continuously flow-efficient, large-bore connection between the sealing balloon element and a volume source in which the pressure is kept constant represents the required synchronicity between the patient's thoracic respiratory activity and the volume flow that is needed to obtain the tracheal seal.

Quick shifts in volume are permitted in the claimed combination of a catheter and a regulator, e.g. by gravity- or spring-powered regulators, which function in the range of low, physiologically harmless pressures, i.e. in a pressure range of ca. 25 to 35 mbar, and do not require unphysiologically high pressure gradients that force the volume flow in order to ensure sufficient volume flows over the connecting supply line between the cuff and regulator.

The regulator can be configured according to the design described in PCT/EP/2013/056169, for instance. The present invention is preferably designed for this simple form of control by a communicating system of interior spaces under isobaric pressure in the physiological pressure range of 20 to 50, preferably 20 to 35 mbar.

The claimed optimized volume flow between the trachea-sealing balloon body and the extracorporeal regulator can also be achieved with tracheal tubes and tracheostomy cannulas of a conventional design, insofar as the supplying feed channel has a flow-affecting cross-sectional area that corresponds to a circular cross section with a circular diameter of at least 2 mm and preferably a circular diameter of 4 to 6 mm. In products with a convention design, the volume-supplying channel is usually circular and has an inner diameter of ca. 0.5 to 0.7 mm. The channel is extruded into the shaft wall of the tube shaft. It transitions outside the shaft into a tube line, which is normally connected to a one-way valve. For the purpose of the thinnest-walled shafts possible and/or in order to permit the largest possible inner diameter of the ventilation lumen, the supply lines in the shaft wall are kept correspondingly low-caliber.

The principle of flow-optimized volume compensation described above can similarly be applied to the dynamic tamponade of the esophagus of a spontaneously breathing patient. The pressure fluctuations in a tamponade balloon placed in the esophagus, which correspond to independent breathing, are usually more pronounced than in a balloon placed in the trachea. They generally conform to the prevailing absolute intrathoracic pressure. To produce a balloon tamponade in the esophagus that seals as efficiently as possible, it is proposed that the balloon be segmented so that it corresponds to the trachea. While the distal segment of the balloon, which actually seals the esophagus, extends over the extent of the esophagus between its upper and lower sphincters, a tapering balloon segment attaches in the proximal direction and optionally extends to the proximal end of the catheter supporting the balloon. The diameter ratios that are hereafter represented on the ventilation catheter and that define the resulting gap between the shaft and the proximal balloon segment can also be applied in the case of gastric tubes for nutrition and/or decompression. Here, too, the shaft of the gastric tube can consist of a single-lumen, thin-walled tube that is corrugated, entirely or in segments, to improve the bending mechanics. The connection to an isobaric volume reservoir can occur in the manner according to the invention, similarly to the tracheal tube.

BRIEF DESCRIPTION OF THE DRAWINGS

Further features, details, advantages and effects based on the invention arise from the following description of preferred embodiments of the invention and with the aid of the accompanying drawings.

FIG. 1 shows a claimed tracheal tube in combination with an external volume-regulating device.

FIG. 3 shows a tracheal tube with multiple volume-shifting supply lines arranged in or on the catheter shaft.

FIG. **3*a* shows a cross-section of the supplying, shaft-integrated lumens of the tube described in FIG. 3**.

FIG. 4 shows a particular embodiment of the tube shown in FIG. 1, in which the trachea-sealing balloon extends beyond the glottis plane.

Figure 5:
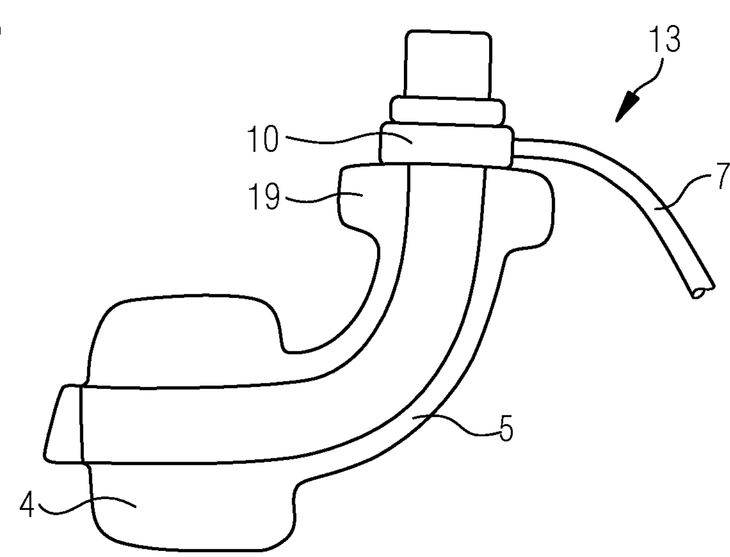

FIG. 5 shows an illustrative embodiment of a claimed tracheostomy cannula.

Figure 6:
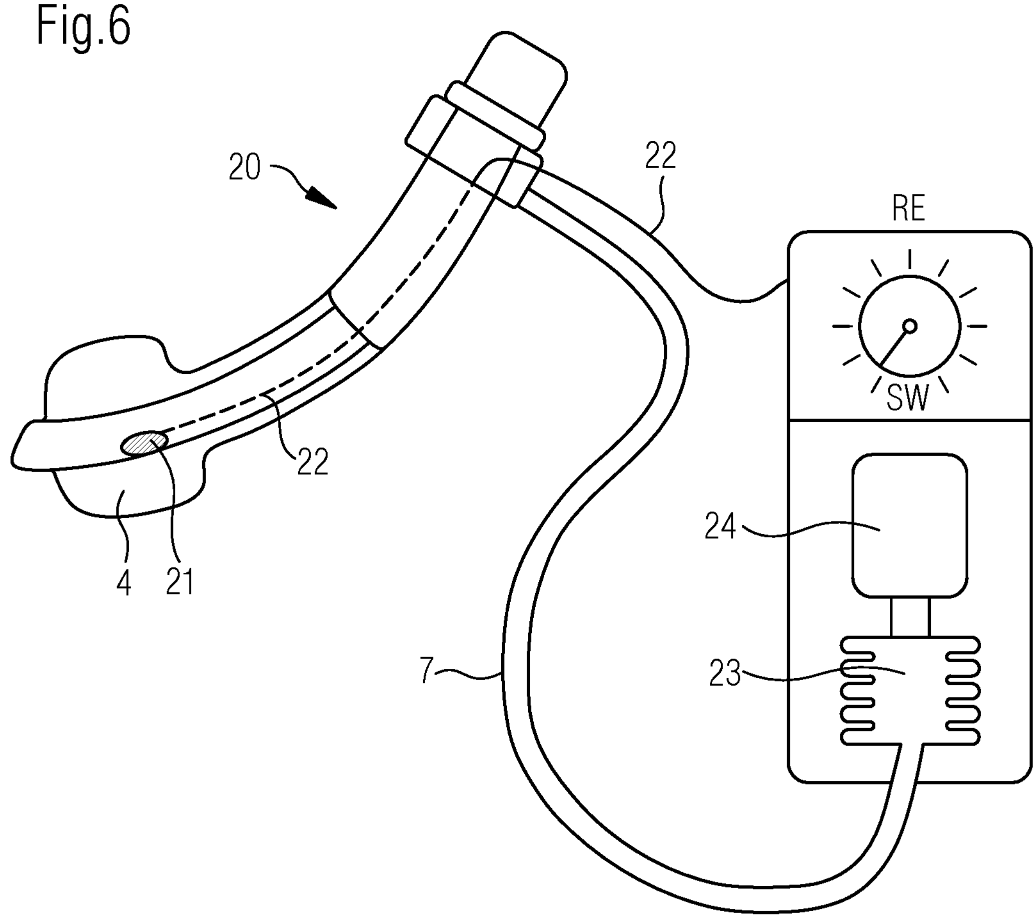

FIG. 6 shows a claimed tracheal tube with a sensor element in the region of the trachea-sealing balloon segment and a regulator unit that is arranged with a sensor in a control loop.

Figure 7:
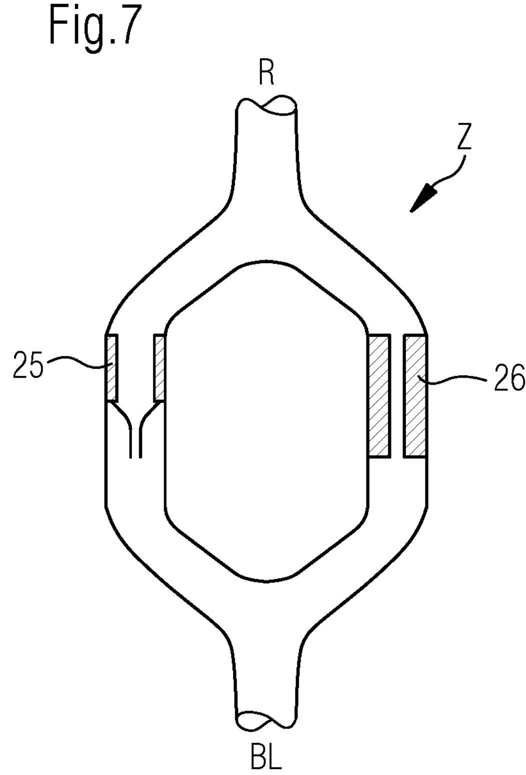

FIG. 7 shows a combined valve/throttle mechanism which prevents the balloon from quickly emptying into the regulator/reservoir, which would be critical for the seal.

Figure 8:
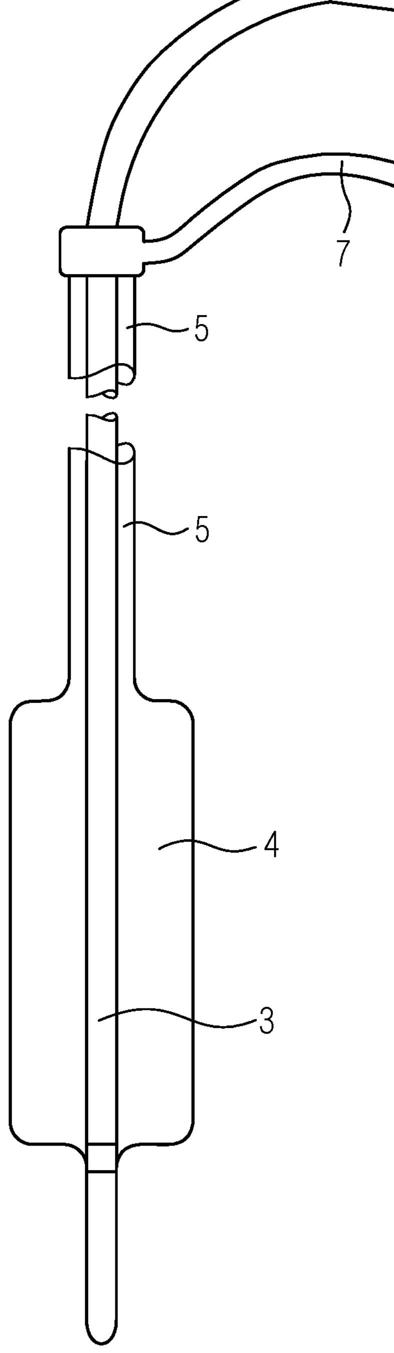

FIG. 8 shows a gastric tube with a proximally extended balloon segment for the dynamically sealing tamponade of the esophagus in combination with an extracorporeal isobaric volume reservoir.

Figure 9:
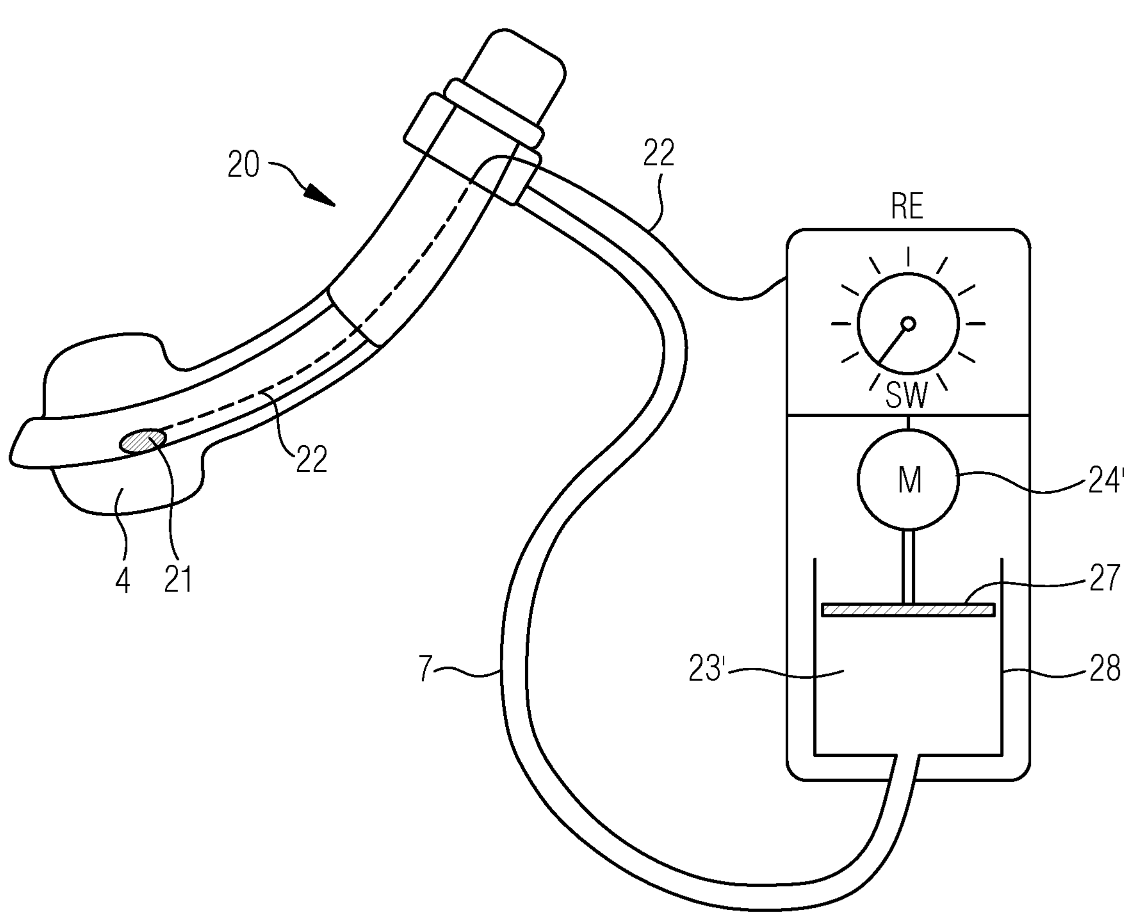

FIG. 9 shows another embodiment of the present invention in a representation according to FIG. 6.

Figure 10:
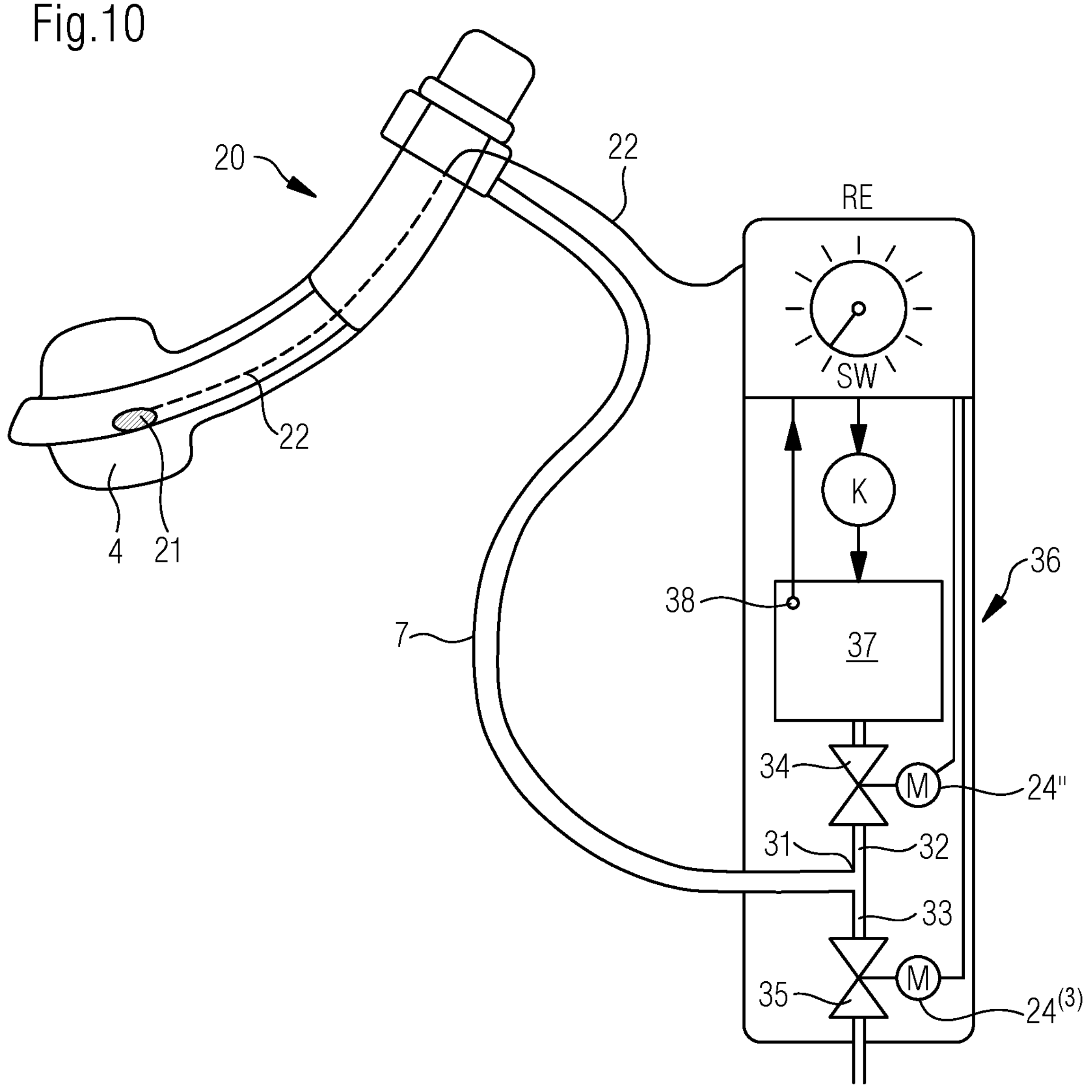

FIG. 10 shows still another embodiment of the present invention in a representation according to FIG. 6.

FIG. **11*a*** shows the characteristic equation of a PD controller which can be used together with the present invention.

FIG. **11*b* shows the electronic circuit diagram of the PD controller which has the characteristic equation of FIG. 11*a***.

FIG. **11*c* shows the step response of the PD controller with the electronic circuit according to FIG. 11*b***.

FIG. **11*d* shows the relation between the parameters of the characteristic equation according to FIG. 11*a* and the elements of the electronic circuit according to FIG. 11*b***.

DETAILED DESCRIPTION OF THE PREFERRED EMBODIMENTS

FIG. 1 describes, in an illustrative total overview, the communicating connection/coupling of a claimed device 1, in the form of a tracheal tube, with a preferably gravity- or spring-driven, isobaric volume reservoir 2.

The supply chamber formed by the freely communicating coupling of the tracheal tube and volume reservoir 2 consists of the trachea-sealing balloon segment 4, the tube-like tapered balloon end 5 that connects in the proximal direction, the supply lumen(s) in the proximal shaft element 6, the flexible supply line 7 to the reservoir that attaches to the shaft as well as the reservoir volume 8 of the regulator.

The distal shaft segment of the tube 3 supports a trachea-sealing balloon 4 at its distal end, said balloon being sealingly attached at its distal end **9*a* to the surface of the shaft. A tube-like proximal balloon segment 5, which tapers relative to the diameter of the sealing balloon segment 4, attaches to the balloon segment 4 in the proximal direction. Its proximal end locks tightly to the surface of the distal end 9*b* of the proximal shaft element 6**.

If a decrease in intrathoracic pressure occurs during the course of inhaling (inspiration), and thus a corresponding transient widening of the tracheal cross-section, which in turn causes a corresponding drop in pressure within the balloon body placed in the trachea, volume flows from the reservoir 2 to the sealing balloon segment 4, wherein the reservoir continuously charges the volume with a defined pressure. As a result, the tracheal sealing pressure can be maintained even when the patient inhales deeply, with a possible pressure drop in the thorax and/or in the trachea-sealing balloon to sub-atmospheric levels, without relevant losses in the sealing capacity.

In a preferred embodiment, the reservoir 2 consists of a reservoir body 8, which can be configured e.g. as a balloon or bellows, and establishes a constant isobaric pressure in the supply chamber by a force K acting on the reservoir.

Crucial to achieving the smallest possible time latency between the initial widening of the tracheal cross-section or the initial reduction of the transmural thoracic forces acting on the tracheal sealing balloon and the start of a seal-creating shift of filling medium to the trachea-sealing balloon segment is, above all, the flow-affecting cross-sectional area of the gap S available the between the distal shaft segment 9 and the proximal extension 5 of the balloon.

In the following figure, the invention proposes especially advantageously dimensioned ratios of the cross-sectional area S to the cross-sectional area of the ventilation lumen ID and to the overall cross-sectional area OD of the catheter between the proximal shaft 6 and the trachea-sealing balloon segment 4.

Figure 2:
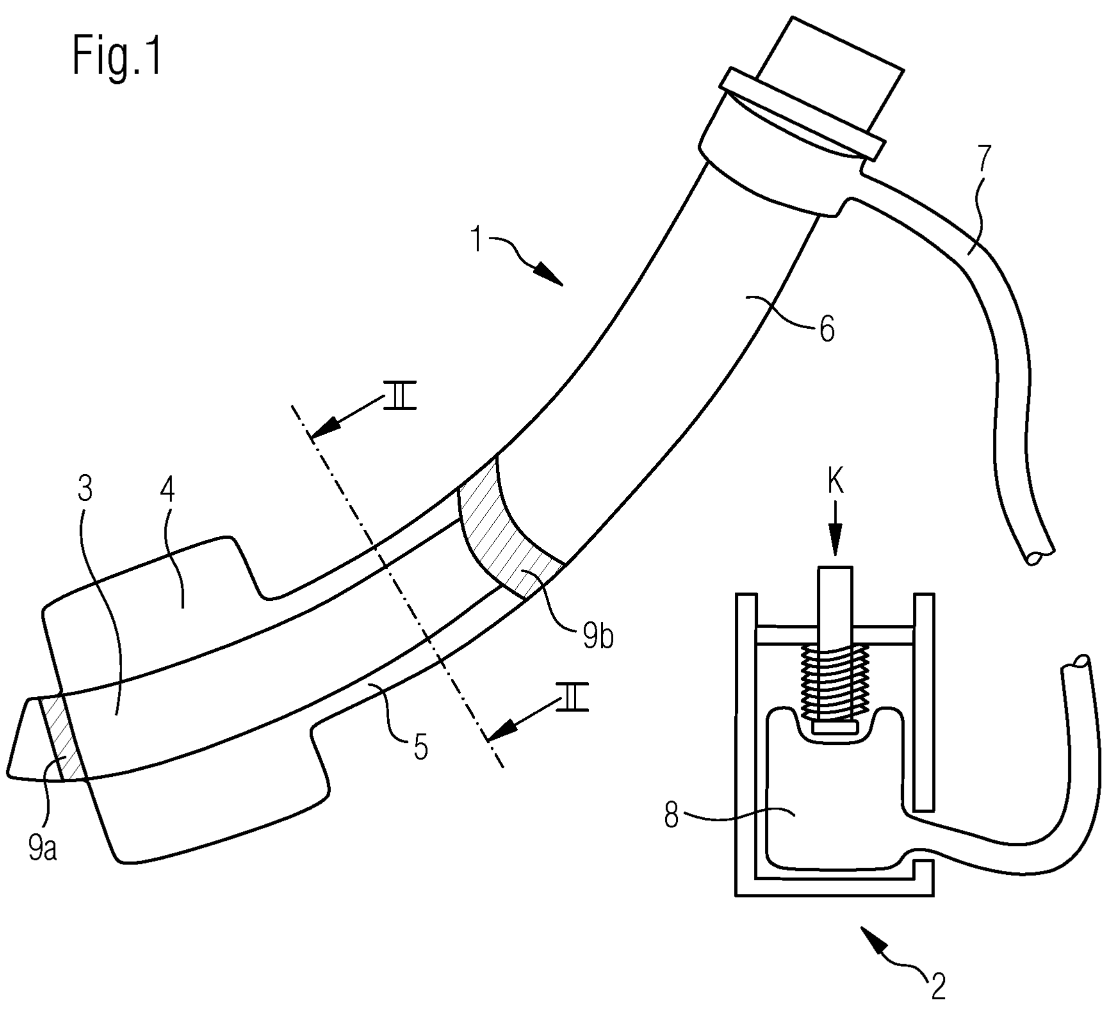
FIG. 2 shows the volume-shafting gap S relative to the overall diameter G in the vicinity of the proximal balloon extension.

FIG. 2 shows a cross-section through the volume-supplying segment 5 of the balloon of the tracheal tube pictured in FIG. 1, said segment attaching to the trachea-sealing balloon in the proximal direction.

S designates the gap surface that is preferred for the supply of filling medium to the balloon. It is defined as the difference between the cross-sectional area G, which is delimited by the sleeve wall of the supplying balloon end 5, and the cross-sectional area OD of the shaft body, which is delimited by the outer surface of the shaft. Here the cross-sectional area S should be 1/10 to 5/10 of cross-sectional area G, especially preferably 2/10 to 3/10 of cross-sectional area G.

Relative to the cross-sectional area ID of the inner lumen of the shaft body, cross-sectional area S should amount to 2/10 to 6/10 of cross-sectional area ID, especially preferably 3/10 to 4/10 of cross-sectional area ID.

In addition to air as the preferred medium, liquid media can also be used to fill the trachea-sealing system.

For the quantitative calculation of the flow conditions in the volume-conducting interior space of the balloon, in particular based on the pressure ratios in the trachea-sealing balloon segment 4, the following place-holder values should be used:

$V_i$ Volume of the distal balloon segment 4

$p_i$ Pressure in the distal balloon segment 4

$\rho_i$ Filling density in the distal balloon segment 4

$M_1$ Air mass in the distal balloon segment 4

$V_2$ Volume of the extracorporeal reservoir 8

$P_2$ Pressure in the extracorporeal reservoir 8

$\rho_2$ Filling density in the extracorporeal reservoir 8

$m_2$ Air mass in the extracorporeal reservoir 8

The following applies for air masses $m_1$, $m_2$:

$$m_1(t) = m_{1,0} + \int_{T=0}^{T=t} S_{m,1}(T)dT \tag{1}$$

$$m_2(t) = m_{2,0} - \int_{T=0}^{T=t} S_{m,2}(T)dT \tag{2}$$

$S_{m,v}$ stands for the air flow to the respective balloon 4, 8 as an air mass flow.

According to the Hagen-Poiseuille equation, the following is true for the mass fluid flow through a line with a circular cross-section and with an inner radius R and length I:

$$S_{m,1} = \frac{\rho_1 \cdot \pi(p_2 - p_1) \cdot R^4}{8\, \eta \cdot I} \tag{3a}$$

$$S_{m,2} = \frac{\rho_2 \cdot \pi(p_1 - p_2) \cdot R^4}{8\, \eta \cdot I} \tag{3b}$$

If, however—as in this case—the secondary lumen represents an annular structure around a primary lumen, then the Hagen-Poiseuille formula does not exactly apply.

Instead, one must consider a space with a strip-like cross-section, which can ideally be imagined in a straightened form, i.e. having a flat structure or a rectangular cross-section with length L and thickness D, i.e. with a cross-sectional area Q=L·D.

Between two plates at a distance D, the following applies for the distribution of the flow rate v(x) along a direction x perpendicular to the plates:

$$v(x) = \frac{(p_1 - p_2) \cdot (D^2/4 - x^2)}{2\, \eta \cdot I} \tag{4}$$

This is a parabolic curve. By integration over cross-sectional area Q, the mass flowing through cross-sectional area Q during time t can be determined:

$$S_{m,1} = \frac{\rho_1 \cdot (p_2 - p_1) \cdot L \cdot D^3}{12\, \eta \cdot I} \tag{5a}$$

$$S_{m,2} = \frac{\rho_2 \cdot (p_1 - p_2) \cdot L \cdot D^3}{12\, \eta \cdot I} \tag{5b}$$

In any case, these formulas replace the above Hagen-Poiseuille formulas (3a) and (3b) for annular balloon segment 5.

Here η stands for the dynamic viscosity of the flowing gas. For air:

η is 17.1 μPa·s at 273 K.

Furthermore, because of the thermal equation of state of ideal gases, the following applies in the balloon 4:

$$\eta_1 = \rho_1 \cdot R_S \cdot T_1 \tag{6a}$$

and in balloon 8:

$$\eta_2 = \rho_2 \cdot R_S \cdot T_2 \tag{6b}$$

In this case, $R_S$ is the individual or specific gas constant, which for air has the value 287.058 J/(kg*K).

$T_v$ is the temperature in balloon sections 4 and 5 and in the balloon 8.

For a temperature of 23° C. or 296 K, the factor $$k = R_{S,air} \cdot T_{23^\circ C.} = 85 \cdot 10^3\ \mathrm{J/(kg \cdot K)} \tag{7}$$

It should be assumed hereafter that the temperature both in balloon 4 and in balloon 8 is I constant 23° C.

$$T_1 = T_2 = 296 \text{ K}.$$

Then the following applies:

$$p_1 = \rho_1 \cdot k \tag{8}$$

$$p_2 = \rho_2 \cdot k \tag{9}$$

Thus by inserting equation (5a) into equation (1), the result is:

$$m_1(t) = m_{1,0} + \int_{T=0}^{T=t} \frac{\rho_1 \cdot L \cdot D^3}{12\eta \cdot I}(p_2 - p_1)dT \tag{10}$$

With equation (8), it follows that:

$$m_1(t) = m_{1,0} + \int_{T=0}^{T=t} \frac{\rho_1 \cdot L \cdot D^3}{12\eta \cdot I \cdot k} p_1(p_2 - p_1)dT \tag{11}$$

Moreover, the following applies in balloon 4:

$$\frac{m_1}{V_1} = \rho_1 = \frac{p_1}{k} \tag{12}$$

Therefore, the following can be written in equation (11) for mass $m_1$:

$$m_1 = \frac{V_1 \cdot p_1}{k} \tag{13}$$

The result:

$$\frac{V_1}{k} \cdot p_1(t) = \frac{V_1}{k} \cdot p_{1,0} - \int_{T=0}^{T=t} \frac{L \cdot D^3}{12\eta \cdot I \cdot k} \cdot \left[p_1^2 - p_1 p_2\right] dT \tag{14}$$

The entire equation can be shorted to V1/k. A differentiation on both sides results in:

$$\frac{dp_1}{dt} = -\frac{L \cdot D^3}{12 V_1 \eta I} \cdot \left[p_1^2 - p_1 p_2\right] \tag{15}$$

This is a Bernoulli differential equation in the form:

$$x' = -a \cdot x \cdot (x - b), \tag{16}$$

wherein $$a = \frac{L \cdot D^3}{12 V_1 \eta I} \tag{17}$$

-continued $$b = p_2 \tag{18}$$

Hereafter it should be assumed that balloon 8 is significantly larger than balloon 4:

$$V_2 \gg V_1$$

From this it follows that the pressure $p_2$ in balloon 8 remains nearly, even when pressure $p_1$ in balloon 4 briefly changes. Under this assumption, the coefficients a and b from Bernoulli differential equation (16) are constant, and the solution to the Bernoulli differential equation is:

$$x(t) = \frac{b}{1 - e^{-abt - bc_1}} \tag{19}$$

The constant of integration $c_1$ can be determined as follows:

$$p_1(t) = \frac{p_2}{1 - e^{-ap_2 t - p_2 c_1}} \tag{20}$$

For t=0, the following must apply:

$$p_1(t) = p_{1,0} \tag{21}$$

The result:

$$p_{1,0} = \frac{p_2}{1 - e^{-p_2 c_1}} \tag{22}$$

$$\frac{p_2}{p_{1,0}} = 1 - e^{-p_2 c_1} \tag{23}$$

$$e^{-p_2 c_1} = \frac{p_{1,0} - p_2}{p_{1,0}} \tag{24}$$

$$-p_2 c_1 = \ln\frac{p_{1,0} - p_2}{p_{1,0}} \tag{25}$$

$$c_1 = -\frac{1}{p_2} \cdot \ln\frac{p_{1,0} - p_2}{p_{1,0}} = \frac{1}{p_2} \cdot \ln\frac{p_{1,0}}{p_{1,0} - p_2} \tag{26}$$

Inserted into equation (2), this provides:

$$\frac{p_{1(t)}}{p_{1,0}} = \frac{p_2}{p_{1,0} - [p_{1,0} - p_2] \cdot e^{-(\pi R^4 p_2 t)/(8 V_1 \eta l)}} \tag{27}$$

This equation is in the form:

$$\frac{p_1(t)}{p_{1.0}} = \frac{p_2}{p_{1.0} - [p_{1.0} - p_2] \cdot e^{-t/T}} \tag{28}$$

where $$T = (12 \cdot V_1 \cdot \eta \cdot I)/(L \cdot D^3 \cdot p_2) \tag{29}$$

The following applies for minor pressure fluctuations in balloon 4, for example:

$$P_{1.0} \approx 0.9 p_2$$

Moreover, for t=τ:

$$e^{-t/T} = e^{-1} \approx 0.368 = k_1$$

Additionally, for t=2τ:

$$e^{-t/T} = e^{-2} \approx 0.135 = k_2$$

And for t=4τ:

$$e^{-t/T} = e^{-4} \approx 0.018 = k_4$$

In equation (28) this yields:

$$\frac{p_1(t = vT)}{0.9\ p_2} = \frac{p_2}{0.9\ p_2 - (0.9\ p_2 - p_2) \cdot k_v}$$

and $$\frac{p_1(t = vT)}{0.9\ p_2} = \frac{p_2}{(0.9 + 0.1 \cdot k_v) \cdot p_2}$$

The result:

$$p_1(t = T) = p_2 \cdot \frac{0.9}{0.9 + 0.1 \cdot 0.368} \approx 0.96 \cdot p_2$$

The control deviation of approximately 0.04••$p_2$ remaining after t=τ corresponds to 40% of the initial deviation of 0.10••$p_2$.

$$p_1(t = 2T) = p_2 \cdot \frac{0.9}{0.9 + 0.1 \cdot 0.135} \approx 0.98 \cdot p_2$$

The control deviation of approximately 0.02••$p_2$ remaining after t=2τ corresponds to 20% of the initial deviation of 0.10••$p_2$.

$$p_1(t = 4T) = p_2 \cdot \frac{0.9}{0.9 + 0.1 \cdot 0.018} \approx 0.99 \cdot p_2$$

The control deviation of approximately 0.01••$p_2$ remaining after t=4τ corresponds to 10% of the initial deviation of 0.10••$p_2$.

When applied within the framework of thoracic respiration, it should be noted that a breathing cycle lasts about 3 sec. So that the cuff does not become leaky over the course of a thoracic breathing cycle, this compensation time should be $t_a$=vτ=20 ms, wherein, with the parameter v, it is possible to choose how good the compensation should be after 20 ms.

This results in τ=20 ms/v.

The minimal result to be sought for v=1 and $t_a$=20 is provided as follows:

From this comes:

$$T = 20 \cdot 10^{-3}\ \text{s} = \frac{12 \cdot 5 \cdot 10^{-6}\ \text{m}^3 \cdot 0.2\ \text{m} \cdot 17.1 \cdot 10^{-6}\ \text{Pas}}{L \cdot D^3 \cdot 10^5\ \text{Pa}}$$

In the process, it was assumed:

$$V_1 = 5\ \text{cm}^3$$

$$I = 20\ \text{cm}$$

$$p_2 = 10^5\ \text{Pa}$$

This results in:

$$L \cdot D^3 = 10.26 \cdot 10^{-14}\ \text{m}^4,$$

It should hereafter further be assumed that, at most, an interior opening with a maximum diameter of 10 mm, corresponding to a radius of 5 mm, is available in the tracheal tube. If one further disregards the cross-section of the outer surface of tube 3 and balloon 4, then the secondary lumen extends a maximum distance outward, and a medium radius $R_m$ of e.g. 4.8 mm can thus be assumed. From this, it is possible to calculate a circumferential length $L_m = 2 \cdot \pi \cdot R_m$ of approximately 30 mm=$30 \cdot 10^{-3}$ m, and from this results:

$$D^3 = 10.26 \cdot 10^{-14}\ \text{m}^4/L$$

and:

$$D^3 = 102.6 \cdot 10^{-12}\ \text{m}^3/30$$

$$D^3 = 3.42 \cdot 10^{-12}\ \text{m}^3$$

$$D = 1.5 \cdot 10^{-4}\ \text{m} = 0.15\ \text{mm}.$$

The secondary lumen thus has a cross-sectional area Q2 of $$Q_2 = L \cdot D = 30 \cdot \text{mm} \cdot 0.15\ \text{mm} = 4.5\ \text{mm}^2.$$

For cross-sectional area $Q_1$ of the primary lumen, D can be subtracted from the 5 mm maximum radius of the tracheal tube, and the result is 4.8 mm. This corresponds to a cross-sectional area $Q_1$ of $$Q_1 = 4.85\ \text{mm} \cdot 4.85\ \text{mm} \cdot 3.14 = 74\ \text{mm}^2.$$

The overall free cross-section $Q=Q_1+Q_2=78.5\ \text{mm}^2$. This means:

$$Q_2/Q = Q_2/(Q_1 + Q_2) = 4.5/78.5 = 0.06.$$

If a shorter compensation time or better compensation within this compensation time $t_a$ is required, then more stringent requirements arise for the above ratio. Accordingly, the value of 0.06 represents the absolute lower limit, which should never be undercut because this would threaten aspiration. In order to have a safety reserve, at least the following should be selected:

$$Q_2/Q = Q_2/(Q_1 + Q_2) \geq 0.08.$$

Moreover, the extracorporeal supply line 7 was likewise disregarded in the above calculation, although its contribution to flow resistance is not insignificant. It is therefore recommended:

$$Q_2/Q = Q_2/(Q_1 + Q_2) \geq 0.10.$$

If, on the other hand, one sets v=4 and $t_a$=10 ms (i.e. the requirement that the remaining control deviation should be less than 10% after 10 ms), then the following is obtained:

$$T = 10\ \text{ms}/4 = \frac{12 \cdot 5 \cdot 10^{-6}\ \text{m}^3 \cdot 0.2\ \text{m} \cdot 17.1 \cdot 10^{-6}}{L \cdot D^3 \cdot 10^5\ \text{Pa}} = \text{Pas}\ \ 25 \cdot 10^{-4}\ \text{s}$$

This then results in:

$$L \cdot D^3 = 82.08 \cdot 10^{-14}\ \text{m}^4,$$

$$D^3 = 82.08 \cdot 10^{-14}\ \text{m}^4/L$$

or, when L=30 mm:

$$D^3 = 27.4 \cdot 10^{-12}\ \text{m}^3$$

$$D = 3 \cdot 10^{-4}\ \text{m} = 0.3\ \text{mm}.$$

The secondary lumen thus has a cross-sectional area $Q_2$ of $$Q_2 = L \cdot D = 30 \cdot \text{mm} \cdot 0.3\ \text{mm} = 9\ \text{mm}^2.$$

For the cross-sectional area $Q_1$ of the primary lumen, D can be subtracted from the 5 mm maximum radius of the tracheal tube, and the result is then 4.6 mm. This corresponds to a cross-sectional area $Q_1$ of $$Q_1 = 4.6\ \text{mm} \cdot 4.6\ \text{mm} \cdot 3.14 = 66\ \text{mm}^2.$$

The overall free cross-section $Q=Q_1+Q_2=75\ \text{mm}^2$. This means:

$$Q_2/Q = Q_2/(Q_1 + Q_2) = 9/75 = 0.12.$$

FIG. 3 describes an embodiment of the shaft body 3 that is integrated into the shaft wall, has one or more volume-supplying channels with a volume-shifting overall cross-section that corresponds in its flow mechanics with the ratios represented in FIG. 2. Here the shaft body preferably consists of multi-lumen extruded tube material which, in addition to a central lumen for ventilation, contains supply lumens disposed around said central lumen. In one such multi-lumen embodiment, the individual lumens can be bundled or combined at the proximal shaft end by an annular structure 10.

FIG. 3*a* shows an illustrative shaft cross-section with multi-lumen volume supply lines 11.

FIG. 4 shows an embodiment variant in which the trachea-sealing balloon segment 4 is extended proximally up to or beyond the plane of the vocal folds GL. This embodiment, in which the balloon segment that is elongated in this way protrudes proportionally from the thorax and is thus not exposed to fluctuations in thoracic pressure, permits an especially large balloon volume that is capable of developing a pressure-receiving buffer effect when a reduction in transmural force on the balloon, caused by breathing mechanics, occurs in the distal, tracheal segment of the balloon. The volume reserve created in this way also has a partial buffering effect when no external volume-compensating unit is connected to the tracheal tube.

In addition, owing to the large contact surface with the exposed tracheal, glottic and supraglottic mucous membranes, a maximally elongated migration path for secretions and pathogens contained therein is created.

To facilitate the trans-glottic positioning of the tube, the balloon can be provided with a circular constriction 12 in the region of the vocal cords GL. This constriction additionally allows for the free movement of the vocal folds, largely independent of the prevailing filling pressure in the balloon.

The distal shaft segment is preferably configured as a thin-walled, single-lumen tube that is stabilized by a corrugation in the shaft wall. The distal shaft transitions in the proximal direction into a shaft segment 6 that, as described in FIG. 1, allows for a large-bore supply line to the proximal balloon segment 5. In a preferred embodiment, as described in FIG. 3*a*, the shaft 6 is designed with a multi-lumen profile. The multi-lumen shaft segment 6 is configured to be stable enough to serve as a bite guard, which prevents a lumen-sealing closure of the ventilation lumen.

The supplying lumens that are integrated into the shaft 6 can be bundled by a terminal element 10 at the proximal end of the tube. In turn, the connection element 7 is attached to a reservoir with a sufficiently large-bore connection.

The thin-walled, single-lumen shaft body 3 is equipped with a wavy corrugation to stabilize the shaft lumen and to permit the largely tension-free axial bending of the shaft. In the preferred embodiment, it should be possible in this way to bend the shaft from 90 to 135 degrees without relevant lumen constriction and without elastic restoring forces acting upon the tissue.

For inner shaft diameters of 7 to 10 mm in the combination of a wall thickness of ca. 0.4 mm, a Shore hardness value of 95 A, a peak-to-peak wave distance of 0.5 mm and a wave amplitude of 0.75 mm, it is possible to produce a correspondingly kink-resistant lumen- and flow-optimized shaft.

In the case of the corrugated embodiment of the shaft 3, when an exchangeable inner cannula is used, such as those that are conventional in tracheostomy cannulas, it is possible to use an inner cannula with a congruently corrugated profile with a corrugation that optimally conforms to the corrugation of the outer cannula and advantageously stabilizes the outer cannula.

FIG. 5 shows an illustrative application of the flow-optimized embodiment of the supplying lumen to the trachea-sealing balloon element 4 in a tracheostomy cannula 13. Similar to the embodiment of tracheal tubes, the volume-supplying balloon end 5 here is led to the surgically created stoma to the trachea and applied to a connector 10 below the cannula flange. The cross-sectional area G of the supplying end 5 can be selected such that, beyond the claimed requirements of a fast volume flow, it is suitable to seal the stoma and thus prevent the escape of secretions. The proximal balloon end 19 can also advantageously be configured as a bulge-like widening, which lies sealingly against the stoma directly below the cannula flange.

FIG. 6 shows a tracheal tube 20, which is provided in the region of the trachea-sealing balloon segment 4 with a pressure-sensitive or pressure-measuring sensor element 21. In a preferred embodiment, the pressure sensor is an electronic component that relays its measurement signal to an electronically controlled regulator RE via a cable line 22. The sensor element 21 preferably consists of an absolute pressure sensor. For example, sensors based on strain gauges or piezoelectric sensors can be used.

The input signal e(t) of the regulator RE is the difference between the filling pressure actually measured by the sensor element 21 in the region of the intracorporeal sealing balloon segment 4 and a setpoint value adjustable via an extracorporeal setting control element SW.

The output signal y(t) of the regulator RE is fed as a corrective signal to a drive element 24 which acts on a bellows-like reservoir 23 in order to increase or decrease the volume thereof. The drive element 24 can consist of a step motor or can be configured as a linear magnetic drive.

The control function of the regulator RE is designed in such a way that the bellows-like reservoir 23 actuated by the drive element 24 according to the regulator output signal y(t) either shifts volume to the intracorporeal sealing balloon 4 by decreasing the volume of the bellows-like extracorporeal reservoir 23, or removes volume from the intracorporeal sealing balloon 4 by increasing the volume of the bellows-like extracorporeal reservoir 23.

The primary object of the regulator RE is to keep the actual filling pressure inside of the intracorporeal filling balloon as constant as possible at the setpoint value SW. The intracorporeal sealing balloon 4 as the controlled process unit is exposed to a disturbing signal resulting from the breathing of the patient, whereby the internal cross-section of the trachea changes. Therefore, two different conditions can be distinguished regarding the control loop: Between two breathing cycles, the filling pressure inside of the sealing balloon 4 can be stabilized at an adjusted setpoint value SW.

In this control method, the sealing balloon pressure is stabilized at a point before a mechanical breath commences and before an actual volume flow of breathing gas into the patient's lungs. This is relevant especially in patients who, for example, must expend increased breathing effort after a long period of controlled machine-assisted ventilation in order to stretch an insufficiently elastic lung in the thorax to a point that triggers a volume flow of breathing air into the lung.

Once the breathing commences, there is a phase of an "isometric" tension of the lung within the thorax and thus of the accompanying decrease in pressure within the thorax, and due to such a pressure decrease, drops in the filling pressure of the intracorporeal sealing balloon 4 can occur which can be critical to the seal. In clinically apneic patients, i.e. patients who can perform (isometric) breathing but do not produce a perceptible breathing gas stream, the described sensor technology also makes it possible to ensure intubation in a manner that prevents aspiration. In the control loop, the breathing-induced pressure fluctuations produce a disturbing signal which has to be compensated by the control loop.

Another disturbing signal may result, if sudden pressure fluctuations occur in the intracorporeal sealing balloon 4, such as when the patient changes positions or suffers a coughing attack. Then, the control loop described has to efficiently and quickly shift volume to the sealing balloon or remove volume from it in a likeweise manner.

In contrast to a regulating reservoir 2, like the one described in FIG. 1 which provides a compensating reserve volume at an isobaric pressure of preferably 20 to 35 mbar, in the electronic regulation within the pressure-generating element 22 of the regulator RE it is possible to build up a pressure that briefly exceeds the tracheally uncritical sealing pressure of 20 to 35 mbar and thereby accelerate the volume flow toward the sealing balloon by means of a corresponding transient pressure gradient. The continuous measurement function of the sensor thereby ensures that the pressure in the balloon does not reach critical levels.

FIG. 9 shows the same or an equivalent tracheal tube 20 as FIG. 6. Especially, in the region of the trachea-sealing balloon segment 4, there is provided a pressure-sensitive or pressure-measuring sensor element 21. The measured signal of this sensor element 21 is fed via a cable 22 or via Bluetooth or by another wireless transmission to the regulator RE. Instead of the bellows-like reservoir 23, the embodiment in FIG. 9 comprises a piston-and-cylinder reservoir 23'. Thereby, a piston 27 is fed displaceable in a longitudinal direction within a cylinder 28 and completes the cylinder 28 as an enclosure of the effectively encircled volume. Thereby, the effective volume of the piston-and-cylinder reservoir 23' is proportional to the displacement of the piston 27 within the cylinder 28, and this displacement can be controlled by a control signal y(t) transmitted to an actuator 24' as a position control signal. In such case, the the effective volume of the piston-and-cylinder reservoir 23' is proportional to the control signal y(t) generated by the control function of the regulator RE.

On the other hand, according to the Hagen-Poiseuille equation, the volume flow rate dV/dt in the pipe connection between the extracorporeal piston-and-cylinder reservoir 23' and the intracorporeal sealing balloon 4 is proportional to the pressure difference Δp between the extracorporeal pressure $p_e = K_M * y(t)$ in the extracorporeal piston-and-cylinder reservoir 23' and the intracorporeal pressure $p_i = (1/Ks) * [e(t) + SW]$ measured in the intracorporeal sealing balloon 4:

$$dV/dt \sim p_e - p_i = K_M{}^* y(t) - (1/K_S)^* [e(t) + SW],$$

wherein $K_M$ is the proportionality factor of the actuator element 24, and $K_S$ is the proportionality factor of the sensor element 23', so that the output signal s(t) of the sensor element 23' is given as:

$$s(t)=K_S{}^*p_i.$$

In FIG. 11_a_, a preferred control function is defined, with a proportional parameter $K_p$ and a derivative parameter $K_d$.

Under static conditions, the derivative term de(t)/dt is zero, and the control function simplifies to:

$$y(t)=K_p{}^*e(t),$$

and this results in:

$$dV/dt\sim p_e-p_i=K_M{}^*K_p{}^*e(t)-(1/K_S)^*[e(t)+SW]=0,$$

$$[K_M{}^*K_p-(1/K_S)]^*e(t)=(1/K_S)^*SW,$$

$$[K_S{}^*K_M{}^*K_p-1]^*e(t)=SW,$$

$$e(t)=[K_S{}^*K_M{}^*K_p-1]^{-1*}SW,$$

$$p_i=(1/K_S)^*[e(t)+SW]=(1/K_S)^*\{[K_S{}^*K_M{}^*K_p-1]^{-1}+1\}^*SW,$$

$$p_i=(1/K_S)^*\{(K_S{}^*K_M{}^*K_p)/[K_S{}^*K_M{}^*K_p-1]\}^*SW,$$

$$p_i=\{(K_M{}^*K_p)/[K_S{}^*K_M{}^*K_p-1]\}^*SW,$$

$$p_i=[K_p-1/(K_M{}^*K_S)]^{-1*}SW.$$

This is the stable pressure $p_i$ inside the intracorporeal sealing balloon 4 at an adjusted setpoint value SW.

In case of a disturbation, a control function with only a proportional term $K_p$*e(t) will only achieve a complete compensation after a rather long period, because the desired pressure value $p_i$ adjusted by the setpoint value SW is only reached asymptotically. To provide a rather fast compensation, an additional derivative term is provided according to the control function as disclosed in FIG. 11_a_.

FIG. 11_c_ shows the step response y(t) of such a controller. The derivative term causes a steep rise at the moment where a unit step function is applied as the input signal e(t). After a short time, the derivative portion of the controller's output signal y(t) decreases rapidly and only the constant, proportional portion of the controller's output signal y(t) remains, which is responsible for a stable behaviour of the closed loop.

According to a preferred embodiment, the peak of the output function y(t) at the moment where a unit step function is applied as the input signal e(t) can be more than double the constant value to which the output function y(t) of the controller approaches asymptotically, or even higher, for example more than three times of the constant value, especially more than four times of the constant value. The higher the ratio between the initial peak and the constant value is, the faster is the dynamic of the regulation, and the better is the dynamic sealing effect of the intracorporeal sealing balloon 4 even in the moment of disturbations.

On the other hand, the ratio between the between the initial peak and the constant value is strongly influenced by the ratio of $K_d/K_p$, which is given as:

$$K_d/K_p=R1^*Cd.$$

As the resistor R1 is given by the above mentioned relation between $p_i$ and SW, the ratio between $K_d$ and $K_p$ has to adjusted via the capacitor Cd.

For example, in order to reach a ratio of $K_d \geq 2{}^*K_p$, the Capacitor Cd should be dimensioned as follows:

$$Cd\geq 2^*s/R1,$$

or:

$$Cd\geq 5^*s/R1,$$

or:

$$Cd\geq 10^*s/R1,$$

with s=second.

A circuit diagram with the characteristic function according to FIG. 11_a_ is shown in FIG. 11_b_. One can see an feedback operational amplifier 29, with its positive input + is connected to ground GND, while the output signal y(t) is fed back to the negative input − via a resistor R2.

The input signal e(t) is derived via a subtracter 30 as a difference between the sensor output signal s(t) and the adjusted setpoint value SW. On the other hand, this input signal e(t) is fed via a parallel circuit of a resistor R1 and a capacitor Cd to the negative input—of the operational amplifier 29.

The parameters $K_p$ and $K_d$ of the characteristic function according to FIG. 11_a_ are related to the resistors R1, R2 and the capacitor Cd of the circuit shown in FIG. 11_b_ by two equations given in FIG. 11_d_.

According to FIG. 7, in order to avoid larger deflations of the tracheal balloon segment or balloon 4 into the reservoir 23, 23', which would be critical for the seal, such as those that can occur when the patient coughs or clenches, the connecting supply line Z between the balloon 4 and the regulator RE can be provided with a large-bore, flow-directing valve 25, which prevents the backflow of filling medium from the balloon BL to the reservoir R. A throttle element 26 that is not flow-directing is arranged in parallel thereto to permit the slow exchange of volume between the balloon and reservoir.

FIG. 10 discloses a still different embodiment of the invention. While the tracheal tube 20 itself and the regulator RE are the same or equivalent to those as shown in FIG. 6 or 9, especially equipped with a pressure-sensitive or pressure-measuring sensor element 21 like that disclosed in FIGS. 6 and/or 9, the bellows-like reservoir 23 of FIG. 9 and the piston-and-cylinder reservoir 23' of FIG. 9 are replaced by another configuration:

The extracorporeal supply line 7 is connected to a branch piece 31 with at least three branches 32, 33, for example in the form of a T-piece or a Y-piece.

A valve 34, 35 is connected to each of the other branches 32, 33 of the branch piece 31, which are not connected to the extracorporeal supply line 7. Preferably, one or both valves 34, 35 are proportional valves, which can be adjusted continuously between a maximal open position and a maximal closed position.

Each of these two valves 34, 35 is coupled to an actuator 24'', 24$^{(3)}$, which in turn is controlled by the regultor RE.

One valve 35 is open to the environment, and if this valve 35 is opened, the intracorporeal sealing balloon 4 is deflated. The flow rate can be continuously controlled by the valve 35.

The other valve 34 is connected to a pressure source 36, and if this valve 34 is opened, the intracorporeal sealing balloon 4 is inflated. The flow rate can be continuously controlled by the valve 34.

The pressure source is preferably in the form of a reservoir 37 which is connected to a compressor K. In order that the pressure in the reservoir 37 can be regulated to a constant pressure value, a pressure sensor 38 is provided within the reservoir 37.

Preferably, the pressure setpoint value for the control loop for regulating the pressure $p_r$ in the reservoir 37 is adjusted to a value above the setpoint value SW for the pressure $p_i$ inside the intracorporeal sealing balloon 4:

$$SW(p_r) > SW(p_i),$$

for example:

$$SW(p_r) \geq 1.5^{*}SW(p_i),$$

or:

$$SW(p_r) \geq 2^{*}SW(p_i),$$

or:

$$SW(p_r) \geq 3^{*}SW(p_i),$$

or:

$$SW(p_r) \geq 5^{*}SW(p_i).$$

For example, while the setpoint value $SW(p_i)$ for the pressure $p_i$ inside the intracorporeal sealing balloon 4 may be in the range from 20 to 25 mbar, the setpoint value $SW(p_r)$ for the pressure $p_r$ in the reservoir 37 may be at 40 mbar or above, or may be at 70 mbar or above, or may be at 100 mbar or above, or may be at 150 mbar or above.

Due to a rather dynamic control function, for example according to the PD-controller as disclosed in FIGS. 11*a* to 11*d*, the higher pressure $p_r$ in the reservoir 37 comprises no danger for the pressure $p_i$ in the intracorporeal sealing balloon 4.

FIG. 8 shows a similar application of the described dynamic tamponade, which allows a patient's esophagus to be sealingly closed by means of a fillable balloon element. The sealing balloon segment 4 transitions to a proximally elongated constriction 5 that defines a free gap S in the direction of the shaft element 3 for the flow-efficient shifting of a filling medium. The proximal elongation 5 of the balloon body optionally extends to or beyond the height of the mouth or nose placement. The elongation 5 transitions into a tube line 7 that is configured for an efficient flow and that, in turn, is coupled to a claimed reservoir or is connected to a different claimed regulating mechanism.

With the devices described in the preceding figures for the flow-optimized shift of volume between a trachea- or esophagus-sealing balloon 4 and an extracorporeal regulating reservoir 2, seal-creating volume compensations can take place within a tracheal or esophageal balloon body within 10 to 30 milliseconds, preferably within 10 to 15 milliseconds, after the beginning of a change in intrathoracic pressure.

LIST OF REFERENCE SIGNS

1 Device
2 Reservoir
3 Tube
4 Balloon
5 Proximal tapered balloon end
6 Proximal shaft element
7 Extracorporeal supply line
8 Reservoir volume
9*a* Distal tube end
9*b* Proximal tube end
10 Annular structure
11 Volume supply line
12 Constriction
13 Tracheostomy cannula
19 Proximal balloon end
20 Tracheal tube
21 Sensor element
22 Cable line
23 Reservoir
24 Drive
25 Flow-straightening valve
26 Throttle element
27 Piston
28 Cylinder
29 Operational amplifier
30 Subtracter
31 Branch piece
32 Branch
33 Branch
34 Valve
35 Valve
36 Pressure source
37 Reservoir
38 Pressure sensor
BL Balloon
G Cross-sectional area
GL Vocal fold plane
GND Ground
ID Inner cross-section of the tube
K Force
OD Outer cross-section of the tube
R Reservoir
RE Regulator
S Gap
SW Setpoint value

What is claimed is:

1. A device for dynamically sealing intubation of a hollow organ, the device comprising:

a shaft-shaped tube configured to be inserted into the hollow organ, the shaft-shaped tube having a primary lumen that is configured to provide access through the hollow organ or to the hollow organ; and an intracorporeal sealing balloon that surrounds a distal region of the shaft-shaped tube, wherein the intracorporeal sealing balloon is configured to operate as a cuff that dynamically seals the hollow organ, wherein one or more secondary lumens for filling the intracorporeal sealing balloon are integrated into a wall of a proximal region of the shaft-shaped tube, wherein at an extracorporeal filling tube that communicates with the one or more secondary lumens, a control device regulates a pressure within the intracorporeal sealing balloon such that:

when a volume of the hollow organ increases, a filling medium flows into the intracorporeal sealing balloon to increase a volume of the intracorporeal sealing balloon, and when the volume of the hollow organ decreases, the filling medium flows out of the intracorporeal sealing balloon to decrease the volume of the intracorporeal sealing balloon, wherein a valve is disposed in the extracorporeal filling tube, and wherein the valve permits a flow of the filling medium from an extracorporeal reservoir balloon toward the intracorporeal sealing balloon in the event that the pressure drops.

2. The device according to claim 1, wherein an interior cross-section of the primary lumen (Q1) and a sum of interior cross-sections of the one or more secondary lumens (Q2) is represented by $Q2/(Q1+Q2)\geq 0.06$.

3. The device according to claim 1, wherein the extracorporeal reservoir balloon has a larger volume in a freely deployed state than a volume of the intracorporeal sealing balloon in the distal region of the shaft-shaped tube.

4. The device according to claim 1, wherein the control device is a mechanical control device or an electronic control device.

5. The device according to claim 1, wherein a pressure in the extracorporeal reservoir balloon is actively controlled or regulated.

6. The device according to claim 5, wherein the pressure in the extracorporeal reservoir balloon is actively regulated such that the pressure within the intracorporeal sealing balloon is kept constant.

7. The device according to claim 6, wherein the pressure within the intracorporeal sealing balloon is inputted into a control loop, and wherein the pressure in the extracorporeal reservoir balloon is based on an output of the control loop.

8. The device according to claim 1, wherein the valve is a one-way valve.

9. The device according to claim 8, wherein a flow constriction, which permits only a limited flow in every flow direction, is arranged in the extracorporeal filling tube that communicates with the one or more secondary lumens.

10. The device according to claim 9, wherein the one-way valve and the flow constriction are connected in parallel.

11. The device according to claim 1, wherein:

the valve permits a flow in case of a pressure gradient from the extracorporeal reservoir balloon, and a flow constriction permits a limited flow in every flow direction, and the valve and the flow constriction are arranged in parallel.

12. The device according to claim 1, wherein the control device is an on-off control device.

13. The device according to claim 1, wherein the control device is a continuous control device.

14. The device according to claim 1, wherein an interior cross-section of the primary lumen (Q1) and a sum of interior cross-sections of the one or more secondary lumens (Q2) is represented by $Q2/(Q1+Q2)\geq 0.08$.

15. The device according to claim 1, wherein an interior cross-section of the primary lumen (Q1) and a sum of interior cross-sections of the one or more secondary lumens (Q2) is represented by $Q2/(Q1+Q2)\geq 0.10$.

16. The device according to claim 1, wherein the intracorporeal sealing balloon has a radially widened distal region.

17. The device according to claim 1, wherein an outer diameter of a distal region of the intracorporeal sealing balloon is different than an outer diameter of a proximal region of the intracorporeal sealing balloon.

18. The device according to claim 1, wherein a proximal region of the intracorporeal sealing balloon has a single secondary lumen of the one or more secondary lumens, wherein the single secondary lumen surrounds the primary lumen.

19. The device according to claim 1, wherein a proximal region of the intracorporeal sealing balloon does not extend to the proximal region of the shaft-shaped tube.

20. The device according to claim 1, wherein the intracorporeal sealing balloon ends at an end face of shaft-shaped tube.

21. The device according to claim 20, wherein a minimal overall cross-section of all channels molded into a tube material of the shaft-shaped tube is greater than a maximum cross-section of an annular secondary lumen in a proximal region of the intracorporeal sealing balloon.

22. The device according to claim 1, wherein an annular structure is located in the proximal region of the shaft-shaped tube.

23. The device according to claim 22, wherein a connector for the extracorporeal filling tube is provided on the annular structure.

24. A method for dynamically sealing intubation of a hollow organ, the method comprising:

inserting a device into the hollow organ, the device comprising:

a shaft-shaped tube configured to be inserted into the hollow organ, the shaft-shaped tube having a primary lumen that provides access through the hollow organ or to the hollow organ; and an intracorporeal sealing balloon that surrounds a distal region of the shaft-shaped tube, the intracorporeal sealing balloon configured to operate as a cuff that dynamically seals the hollow organ, wherein one or more secondary lumens for filling the intracorporeal sealing balloon are integrated into a wall of a proximal region of the shaft-shaped tube, wherein at an extracorporeal filling tube that communicates with the one or more secondary lumens, a control device regulates a pressure within the intracorporeal sealing balloon such that:

when a volume of the hollow organ increases, a filling medium flows into the intracorporeal sealing balloon to increase a volume of the intracorporeal sealing balloon, and when the volume of the hollow organ decreases, the filling medium flows out of the intracorporeal sealing balloon to decrease the volume of the intracorporeal sealing balloon, wherein a valve is disposed in the extracorporeal filling tube, and wherein the valve permits a flow of the filling medium from an extracorporeal reservoir balloon toward the intracorporeal sealing balloon in the event that the pressure drops.

* * * * *